United States Patent
Bevins et al.

(10) Patent No.: US 11,034,573 B2
(45) Date of Patent: Jun. 15, 2021

(54) FUEL DELIVERY SYSTEM HAVING CORROSIVE DETECTION ASSEMBLY

(71) Applicant: Veeder-Root Company, Simsbury, CT (US)

(72) Inventors: James T. Bevins, South Windsor, CT (US); Donald Kunz, South Windsor, CT (US); Lawrence Hunter, Canton, CT (US); Kenneth D. Cornett, Simsbury, CT (US); Adriano Baglioni, East Granby, CT (US); Gaston Berrio, Avon, CT (US)

(73) Assignee: VEEDER-ROOT COMPANY, Simsbury, CT (US)

( * ) Notice: Subject to any disclaimer, the term of this patent is extended or adjusted under 35 U.S.C. 154(b) by 0 days.

(21) Appl. No.: 16/116,400

(22) Filed: Aug. 29, 2018

(65) Prior Publication Data

US 2019/0062142 A1     Feb. 28, 2019

Related U.S. Application Data

(60) Provisional application No. 62/551,567, filed on Aug. 29, 2017.

(51) Int. Cl.
*B67D 7/32* (2010.01)
*G01N 17/02* (2006.01)
(Continued)

(52) U.S. Cl.
CPC ............... *B67D 7/32* (2013.01); *B67D 7/04* (2013.01); *B67D 7/342* (2013.01); *B67D 7/68* (2013.01);
(Continued)

(58) Field of Classification Search
CPC .. B67D 7/32; B67D 7/085; B67D 7/00; B67D 7/06; B67D 7/3209; B67D 7/3218;
(Continued)

(56) References Cited

U.S. PATENT DOCUMENTS

| 3,104,355 A | 9/1963 | Holmes et al. |
| 3,936,737 A | 2/1976 | Jefferies, Sr. |

(Continued)

OTHER PUBLICATIONS

International Search Report and Written Opinion dated Nov. 2, 2018 in corresponding international PCT application No. PCT/US2018/048551, all enclosed pages cited.

(Continued)

*Primary Examiner* — Hai Phan
*Assistant Examiner* — Anthony D Afrifa-Kyei
(74) *Attorney, Agent, or Firm* — Nelson Mullins Riley & Scarborough LLP

(57) ABSTRACT

A fuel dispensing system includes a fuel tank adapted to contain a quantity of fuel. A fuel dispenser in is fluid communication with the fuel tank via piping. A pump is operative to transfer fuel from the fuel tank to the fuel dispenser. A corrosive detection assembly operative to identify presence of a corrosive substance in the fuel is also provided. The corrosive detection assembly has at least one thermoelectric detector positioned to be in contact with fuel vapor in the fuel dispensing system, the thermoelectric detector producing a detector signal indicating presence of the corrosive substance. Electronics are in electrical communication with the thermoelectric detector, the electronics being operative to interpret the detector signal and produce an output if the corrosive substance is present. The at least one thermoelectric detector may comprises a plurality of thermoelectric detectors at different locations in the fuel dispensing system.

27 Claims, 7 Drawing Sheets

(51) Int. Cl.
  *B67D 7/34* (2010.01)
  *B67D 7/04* (2010.01)
  *B67D 7/68* (2010.01)
  B67D 7/08 (2010.01)
  G01N 33/28 (2006.01)
(52) U.S. Cl.
  CPC ............. *G01N 17/02* (2013.01); *B67D 7/085* (2013.01); *G01N 33/2847* (2013.01)
(58) Field of Classification Search
  CPC .. B67D 7/3227; B67D 7/3236; B67D 7/3245; B67D 7/3281; B67D 7/34; B67D 7/0498; B67D 7/78; G01N 17/02; G01N 33/2847; C01D 7/00; C01F 11/24; C09K 15/02; B01D 53/261; B01D 53/28; B01D 2253/10; B01D 2253/112; B01D 2253/104; B01D 2253/106; B01D 2253/202
  See application file for complete search history.

(56) References Cited

U.S. PATENT DOCUMENTS

| | | | |
|---|---|---|---|
| 4,186,605 | A | 2/1980 | Bourigault |
| 5,070,024 | A | 12/1991 | Bruno |
| 5,288,147 | A | 2/1994 | Schaefer et al. |
| 5,954,080 | A | 9/1999 | Leatherman |
| 6,258,253 | B1 | 7/2001 | Davis |
| 6,435,204 | B2 | 8/2002 | White et al. |
| 6,946,855 | B1 | 9/2005 | Hemblade |
| 7,034,553 | B2 | 4/2006 | Gilboe |
| 8,291,928 | B2 | 10/2012 | Reid et al. |
| 8,770,237 | B2 | 7/2014 | Bolt et al. |
| 9,428,375 | B2 | 8/2016 | Sabo et al. |
| 9,604,838 | B2 | 3/2017 | Cornett et al. |
| 9,739,512 | B2 | 8/2017 | Rao |
| 2006/0018762 | A1* | 1/2006 | Aisenbrey ........... F04D 29/2227 416/241 A |
| 2007/0131864 | A1* | 6/2007 | Ellis ...................... G01N 21/05 250/343 |
| 2009/0195260 | A1 | 8/2009 | Bell et al. |
| 2009/0311772 | A1* | 12/2009 | Quinn .................... C12M 21/12 435/286.5 |
| 2013/0047963 | A1 | 2/2013 | Horsting |
| 2014/0116138 | A1* | 5/2014 | Sheverev ............. G01N 17/008 73/579 |
| 2014/0202580 | A1 | 7/2014 | Hutchinson |
| 2018/0257925 | A1* | 9/2018 | Schultz ................ B01D 36/006 |

OTHER PUBLICATIONS

Abstract from Department of Energy Technical Report: "Characterization of Corrosion Probe Coupons Exposed in Tank 241-AN-107," dated Dec. 16, 2003, accessed from https://www.osti.gov/biblio/820849 on Mar. 3, 2020, all enclosed pages cited.

Collection of abstracts obtained from "ScienceDirect Topics: Electrical Resistance Probe," dated 2002, 2011, 2014, 2014, 2016, 2017, 2017, 2018, and 2019, accessed from https://www.sciencedirect.com/topics/engineering/electrical-resistance-probe on Mar. 3, 2020, all enclosed pages cited.

Cosasco "High Sensitivity Atmospheric Corrosion Electrical Resistance (ER) Sensor, Model 610" brochure, dated Aug. 28, 2017, all enclosed pages cited.

Cosasco "Electrical Resistance (ER) Probes, Model 2500/2500HT" brochure, dated Jan. 31, 2019, all enclosed pages cited.

Cosasco Press Release "Rohrback Coasasco Systems (RCS) launches new Handheld Portable Corrosion Data Collection system, Checkmate (TM) DL, suitable for data collection in hazardous areas," dated Feb. 6, 2006, all enclosed pages cited.

T.P. Wang, "Thermocouple Materials," ASM International, 1990, all enclosed pages cited.

"Introducing the New Model ECM(TM) Environmental Condition Monitor;" Rohrback Cosasco Systems; Press Release; Aug. 17, 2005.

"Model ER1000 Electrical Resistance Probe with 1/2" NPT Pipe Plug and Loop Element;" Metal Samples; Data Sheet; retrieved Mar. 2020 from https://www.alspi.com/er1000.htm.

"ANSI and IEC Color Codes for Thermocouples, Wire and Connectors;" OMEGA; retrieved Mar. 2020 from https:// assets.omega.com/pdf/test-and-measurement-equipment/temperature/sensors/thermocouple-probes/tc_colorcodes.pdf.

Mar. 31, 2021 Search Report issued in European Patent Application No. 18850412.0; 8 pp.

* cited by examiner

FUEL DELIVERY SYSTEM HAVING CORROSIVE DETECTION ASSEMBLY

PRIORITY CLAIM

This application is based upon and claims the benefit of provisional application Ser. No. 62/551,567, filed Aug. 29, 2017, incorporated fully herein by reference for all purposes.

BACKGROUND

The present invention relates generally to equipment used in fuel dispensing environments. More specifically, the present invention relates to a fuel delivery system having the capability of detecting the presence of corrosives that might lead to reliability and maintenance issues.

As is well known known, liquid fuel delivery systems typically include one or more fuel dispensers located in the forecourt area of a service station. The fuel dispensers are connected via piping with a source of the liquid fuel (e.g., a tank containing gasoline). Typically, the piping is located under the forecourt so as to feed the liquid fuel from an underground storage tank (UST). Multiple USTs may be provided for different types or grades of fuel. Fuel grades can be mixed as necessary or desired to yield still further grades of fuel.

Modern fueling environments may store liquid fuels which are mixtures of gasoline and ethanol in various ratios, rather than "pure" gasoline. For example, E10 is a liquid fuel comprising 90% gasoline and 10% ethanol. As small amounts of water enter the storage tank containing a gasoline/ethanol mixture, the ethanol absorbs the water. Alternative fuels such as low sulfur diesel and biodiesel are also becoming more common.

The introduction of various alternative and pollution reducing fuels (e.g., fuels with ethanol oxygenate) has created the potential for corrosion in fuel dispensing systems (especially when the fuel does not have a biological reducing inhibitor such as sulfur or includes a biologically supportive substance, such as ethanol). When it occurs, corrosion can result in an interruption of fueling operations, loss of sales, and possible damage.

SUMMARY

The present invention recognizes and addresses various considerations of prior art constructions and methods. According to one embodiment, the present invention provides a fuel dispensing system comprising a fuel tank adapted to contain a quantity of fuel. A fuel dispenser is in fluid communication with the fuel tank via piping. A pump is operative to transfer fuel from the fuel tank to the fuel dispenser. A corrosive detection assembly operative to identify presence of a corrosive substance in the fuel is also provided. The corrosive detection assembly has at least one thermoelectric detector positioned to be in contact with fuel vapor in the fuel dispensing system, the thermoelectric detector producing a detector signal indicating presence of the corrosive substance. Electronics are in electrical communication with the thermoelectric detector, the electronics being operative to interpret the detector signal and produce an output if the corrosive substance is present. The at least one thermoelectric detector may comprise a plurality of thermoelectric detectors at different locations in the fuel dispensing system.

In some exemplary embodiments, the thermoelectric detector is located in an upper portion of the fuel tank above a maximum fuel level. In some exemplary embodiments, the pump is a submersible turbine pump (STP) and the thermoelectric detector is located in an STP sump. In some exemplary embodiments, the thermoelectric detector is located in a fuel dispenser sump located below the fuel dispenser.

In some exemplary embodiments, the thermoelectric detector may comprise a sensing circuit having a pair of junctions formed by interconnection of dissimilar conductors, the pair of junctions being configured to experience a substantially equivalent ambient temperature. In some exemplary embodiments, one of the pair of junctions is in direct contact with the vapor environment and another of the pair of junctions is in indirect contact with the vapor environment via a media isolated assembly. The detector signal in such embodiments may originate at the another of the pair of junctions. A second sensing circuit having a pair of junctions formed by interconnection of dissimilar conductors may also be provided, one of the pair of junctions of the sensing circuit and one of the pair of junctions of the second sensing circuit being connected together.

Another aspect of the present invention provides a corrosive detection assembly for use in a fuel dispensing system. The corrosive detection assembly comprises at least one thermoelectric detector positioned to be in contact with fuel vapor in the fuel dispensing system, the thermoelectric detector producing a detector signal indicating presence of the corrosive substance. The thermoelectric detector includes a sensing circuit having a pair of junctions formed by interconnection of dissimilar conductors, the pair of junctions being configured to experience a substantially equivalent ambient temperature. Electronics in electrical communication with the thermoelectric detector are operative to interpret the detector signal and produce an output if the corrosive substance is present.

Another aspect of the present invention utilizes a thermoelectric detector having a plurality of sensing circuits each with a different detection response time. For example, junctions of each such sensing circuit may be made of progressively heavier gage wire such that each heavier gage sensing circuit has a slower response time than the next smaller gage sensing circuit. The difference in time to detection between the sensing circuits is indicative of and related to the severity of the corrosive condition of the environment. That is, shorter detection times indicate higher concentration levels of corrosive substances.

Those skilled in the art will appreciate the scope of the present invention and realize additional aspects thereof after reading the following detailed description of preferred embodiments in association with the accompanying drawing figures.

BRIEF DESCRIPTION OF THE DRAWINGS

A full and enabling disclosure of the present invention, including the best mode thereof directed to one skilled in the art, is set forth in the specification, which makes reference to the appended drawings, in which.

Figure 1:
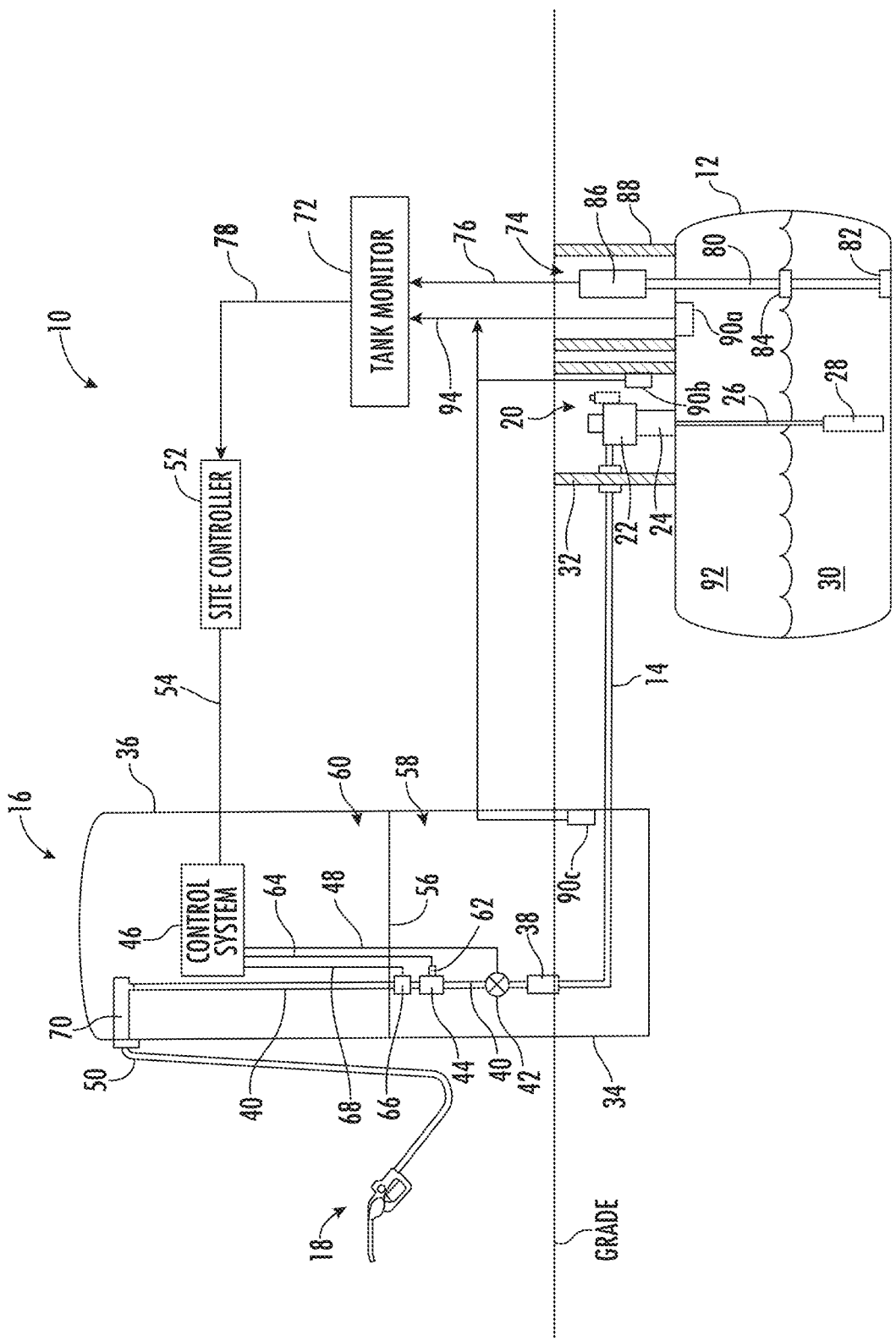
FIG. 1 is a diagrammatic representation of fuel dispensing system including a corrosive detection assembly in accordance with an embodiment of the present invention.

Repeat use of reference characters in the present specification and drawings is intended to represent same or analogous features or elements of the invention.

DETAILED DESCRIPTION OF PREFERRED EMBODIMENTS

Reference will now be made in detail to presently preferred embodiments of the invention, one or more examples of which are illustrated in the accompanying drawings. Each example is provided by way of explanation of the invention, not limitation of the invention. In fact, it will be apparent to those skilled in the art that modifications and variations can be made in the present invention without departing from the scope or spirit thereof. For instance, features illustrated or described as part of one embodiment may be used on another embodiment to yield a still further embodiment. Thus, it is intended that the present invention covers such modifications and variations as come within the scope of the present disclosure including the appended claims and their equivalents.

Certain fueling systems, particularly those that dispense fuel without a biological reducing inhibitor or fuel that includes a biologically supportive substance, may experience excessive or accelerated corrosion. The corrosion is often caused by the presence of bacteria that may be introduced into the fuel from the surrounding environment. For example, the bacteria may react with ethanol in the fuel to produce acid (e.g., acetic acid) that has a deleterious effect on equipment of the fuel dispensing system. Embodiments of this invention provides a corrosive detection assembly that can be used to detect presence of the corrosive substance so that remedial action can be taken.

In this regard, FIG. 1 is a diagrammatic representation of a fuel dispensing system 10 in a retail service station environment according to an aspect of the present invention. In general, fuel may travel from an underground storage tank (UST) 12 via main fuel piping 14, which may be a double-walled pipe having secondary containment as is well known, to fuel dispenser 16 and nozzle 18 for delivery. An exemplary underground fuel delivery system is illustrated in U.S. Pat. No. 6,435,204, hereby incorporated by reference in its entirety for all purposes.

More specifically, a submersible turbine pump (STP) 20 associated with the UST 12 is used to pump fuel to the fuel dispenser 16. (In some embodiments, the fuel dispenser may be self-contained, meaning that fuel is drawn to the fuel dispenser by a pump unit positioned within the fuel dispenser housing.) STP 20 is comprised of a distribution head 22 containing power and control electronics that provide power through a riser 24 down to a boom 26, eventually reaching a turbine pump contained inside an outer turbine pump housing 28. STP 20 may preferably be the RED JACKET® submersible turbine pump, manufactured by the Veeder-Root Co. of Simsbury, Conn. There may be a plurality of USTs 12 and STPs 20 in a service station environment if more than one type or grade of fuel 30 is to be delivered by a fuel dispenser 16.

The turbine pump operates to draw fuel 30 upward from the UST 12 into the boom 26 and riser 24 for delivery to the fuel dispenser 16. After STP 20 draws the fuel 30 into the distribution head 22, the fuel 30 is carried through STP sump 32 to main fuel piping 14. Main fuel piping 14 carries fuel 30 through dispenser sump 34 to fuel dispenser 16 for eventual delivery. Dispenser sump 34 is adapted to capture any leaked fuel 30 that drains from fuel dispenser 16 and its fuel handling components so that fuel 30 is not leaked into the ground.

Main fuel piping 14 may then pass into housing 36 of fuel dispenser 16 through a shear valve 38. As is well known, shear valve 38 is designed to close the fuel flow path in the event of an impact to fuel dispenser 16. U.S. Pat. No. 8,291,928, hereby incorporated by reference in its entirety for all purposes, discloses an exemplary secondarily-contained shear valve adapted for use in service station environments. Shear valve 38 contains an internal fuel flow path to carry fuel 30 from main fuel piping 14 to internal fuel piping 40.

After fuel 30 exits the outlet of shear valve 38 and enters into internal fuel piping 40, it may encounter a flow control valve 42 positioned upstream of a flow meter 44. (In some fuel dispensers, valve 42 may be positioned downstream of the flow meter 44.) In one embodiment, valve 42 may be a proportional solenoid controlled valve, such as described in U.S. Pat. No. 5,954,080, hereby incorporated by reference in its entirety for all purposes.

Flow control valve 42 is under control of a control system 46 via a flow control valve signal line 48. In this manner, control system 46 can control the opening and closing of flow control valve 42 to either allow fuel to flow or not flow through meter 44 and on to the hose 50 and nozzle 18. Control system 46 may be any suitable electronics with associated memory and software programs running thereon whether referred to as a processor, microprocessor, controller, microcontroller, or the like (which are intended herein as equivalent terms). In a preferred embodiment, control system 46 may be comparable to the microprocessor-based control systems used in CRIND and TRIND type units sold by Gilbarco Inc. Control system 46 typically controls other aspects of fuel dispenser 16, such as valves, displays, and the like as is well understood. For example, control system 46 typically instructs flow control valve 42 to open when a fueling transaction is authorized. In addition, control system 46 may be in electronic communication with a site controller 52 via a fuel dispenser communication network 54. Communication network 54 may be any suitable link, such as two wire, RS 422, Ethernet, wireless, etc. as needed or desired. Site controller 52 communicates with control system 46 to control authorization of fueling transactions and other conventional forecourt control activities. For example, the site controller functions may be provided by the PASSPORT® point-of-sale system manufactured by Gilbarco Inc. or by a separate forecourt controller.

The memory of control system 46 (and other memories discussed herein) may be any suitable memory or computer-readable medium as long as it is capable of being accessed by the control system, including random access memory (RAM), read-only memory (ROM), erasable programmable ROM (EPROM), or electrically EPROM (EEPROM), CD- ROM, DVD, or other optical disk storage, solid-state drive (SSD), magnetic disc storage, including floppy or hard drives, any type of suitable non-volatile memories, such as secure digital (SD), flash memory, memory stick, or any other medium that may be used to carry or store computer program code in the form of computer-executable programs, instructions, or data. Control system 46 may also include a portion of memory accessible only to control system 46.

Flow control valve 42 is contained below a vapor barrier 56 in a hydraulics compartment 58 of fuel dispenser 16. Control system 46 is typically located in an electronics compartment 60 of fuel dispenser 16 above vapor barrier 56. After fuel 30 exits flow control valve 42, it typically flows through meter 44, which preferably measures the flow rate of fuel 30. In some embodiments, meter 44 may be capable of measuring the density and/or temperature of the flowing fuel. Flow meter 44 may be any suitable flow meter known to those of skill in the art, including positive displacement, inferential, and Coriolis mass flow meters, among others. Meter 44 typically comprises electronics 62 that communicate information representative of the flow rate, density, and/or temperature of fuel to control system 46 via a signal line 64. For example, electronics 62 may typically include a pulser as known to those skilled in the art. In this manner, control system 46 can update the total gallons (or liters) dispensed and the price of the fuel dispensed on an information display of fuel dispenser 16.

As fuel leaves flow meter 44 it enters a flow switch 66. Flow switch 66, which preferably comprises a one-way check valve that prevents rearward flow through fuel dispenser 16, generates a flow switch communication signal via flow switch signal line 68 to control system 46 to communicate when fuel 30 is flowing through flow meter 44. The flow switch communication signal indicates to control system 46 that fuel is actually flowing in the fuel delivery path and that subsequent signals from flow meter 44 are due to actual fuel flow.

After fuel 30 enters flow switch 66, it exits through internal fuel piping 40 to be delivered to a blend manifold 70. Blend manifold 70 receives fuels of varying octane levels from the various USTs and ensures that fuel of the octane level selected by the customer is delivered. After flowing through blend manifold 70, fuel 30 passes through fuel hose 50 and nozzle 18 for delivery to the customer's vehicle.

UST 12 includes an automatic tank gauge (ATG) system to monitor level of fuel 30. The gauging system includes a tank monitor 72 in electrical communication with a probe 74 (e.g., a magnetostrictive probe) such as via an appropriate signal line 76. In turn, tank monitor 72 is in electrical communication with site controller 52, such as via signal line 78. Preferably, tank monitor 72 is a microprocessor-based system having suitable program instructions stored in memory to perform the desired functions. For example, tank monitor 72 may comprise the TLS-450 or TLS-350 systems manufactured by Veeder-Root Company.

Probe 74 includes a probe shaft 80 that extends through the interior of UST 12, as shown. A water level float 82 and fuel level float 84 are able to slide along the shaft 80 as the liquid levels change. In particular, water level float 82 floats on the water-fuel interface so that the level of water in the bottom of UST 12 can be detected. If the water level exceeds a threshold (such as if it is too near the inlet of pump housing 28), operation of STP 20 can be interrupted. Fuel level float 84 floats on top of fuel 30 so that the amount of fuel in UST 12 can be determined.

As shown, probe 74 includes an electronics head 86 at the end of probe shaft 80, located external to UST 12 in a well 88. Head 86 generates signals provided to tank monitor 72 that are indicative of the locations of floats 82 and 84. In an example embodiment, probe 74 may comprise the Mag Plus magnetostrictive probe system manufactured by Veeder-Root Company.

Fuel dispensing system 10 further comprises a corrosive detection assembly that is operative to detect the presence of a corrosive substance that may otherwise lead to premature corrosion within the fuel dispensing system. As will be explained, the corrosive detection system preferably includes at least one thermoelectric detector 90 situated in an electrolytic vapor environment within the fuel dispensing system. In this regard, evaporation of liquid fuel produces fuel vapor at various locations in the fuel dispensing system. A corrosive substance in the fuel will also be present in the vapor, where it is detected by the thermoelectric detector 90 as described more fully below.

In the illustrated embodiment, for example, a first thermoelectric detector 90a is located in the ullage 92 of UST 12 at a location above the highest expected level of fuel 30. As is well known, hydrocarbon vapors produced by evaporation of fuel 30 will be located in ullage 92. If a corrosive substance is present in the vapor, detector 90a produces a signal that can be detected by suitable circuitry such as suitably programmed circuitry of tank monitor 72. Toward this end, detector 90a is in electrical communication with tank monitor 72 via a corresponding signal line 94. In addition, or in the alternative, one or more thermoelectric detectors may be situated in other locations in the fuel dispensing system. For example, the illustrated embodiment includes a thermoelectric detector 90b in STP sump 32 and/or a thermoelectric detector 90c in dispenser sump 34.

Figure 2:
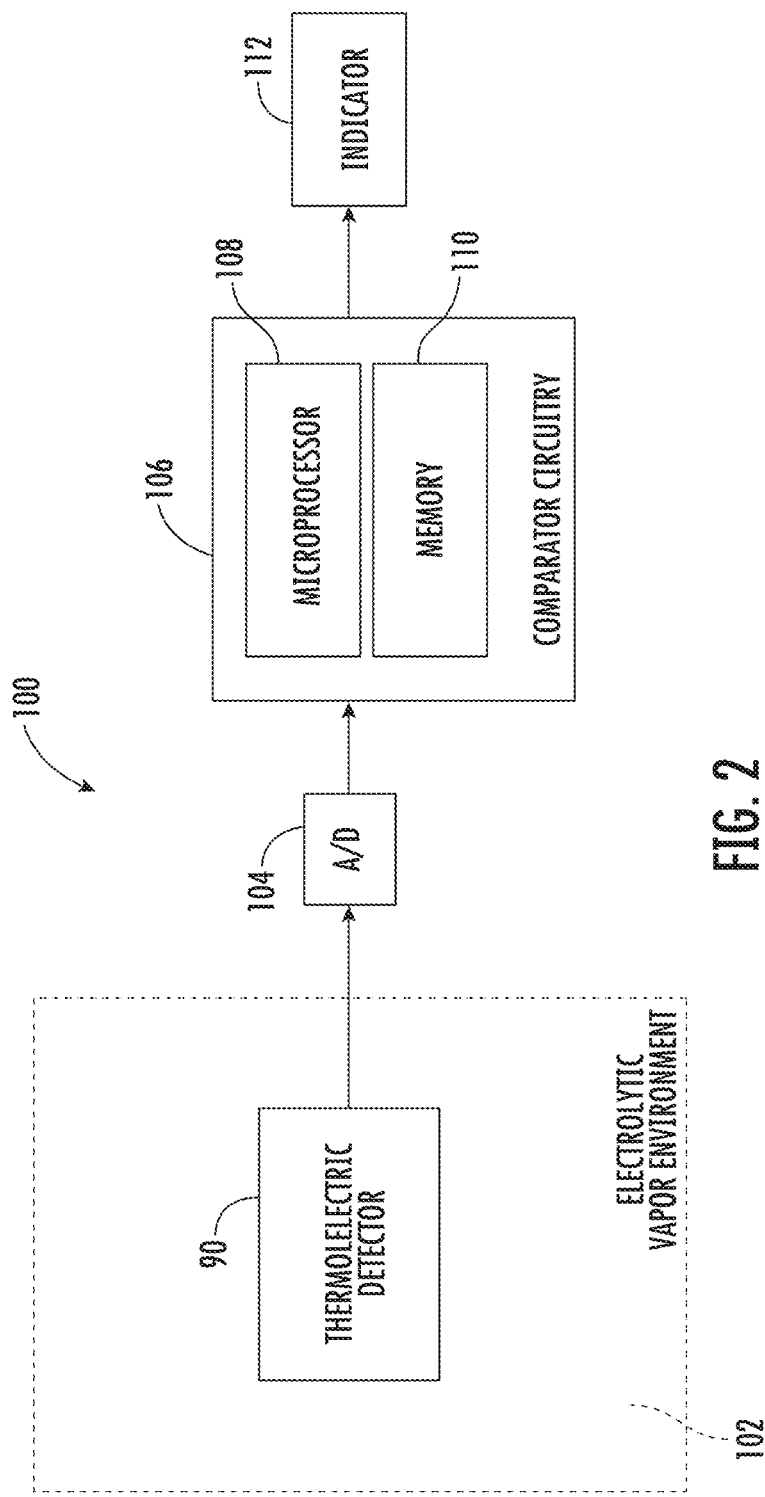
FIG. 2 is a diagrammatic representation showing components of a corrosive detection assembly in accordance with an embodiment of the present invention.

Referring now to FIG. 2, certain additional details regarding an exemplary corrosive detection assembly 100 of the present invention can be most easily explained. As shown, thermoelectric detector 90 is situated in a vapor environment 102, which will be electrolytic in the presence of the corrosive substance. As a result, a signal indicating presence of the corrosive substance will be produced by detector 90. While analog processing is possible within the scope of the present invention, the analog output of detector 90 is sampled and converted to a digital signal in the illustrated embodiment via a suitable analog-to-digital (A/D) converter 104. The output of A/D converter 104 is fed to comparator circuitry 106, which in this embodiment includes a microprocessor 108 and associated memory 110. Microprocessor 108 executes suitable program instructions to interpret the digitized signals from detector 90. If presence of the corrosive is detected, a signal indicative thereof can be provided to indicator 112 which may be any suitable device, circuitry, computer program, or other indicator that can be used to act upon the presence of the corrosive substance. For example, indicator 112 may be a visual or audible indicator to inform an operator that the corrosive material is present. In addition or in the alternative, indicator 112 may comprise a computer program that continuously tracks the amount of corrosive substance and generates action at the appropriate time. As noted above, the circuitry of corrosive detection assembly 100 may be incorporated into tank monitor 72. For example, tank monitor 72 can be programmed to perform the functions described in relation to FIG. 2 in addition to other functions normally performed by tank monitor 72.

Figure 3:
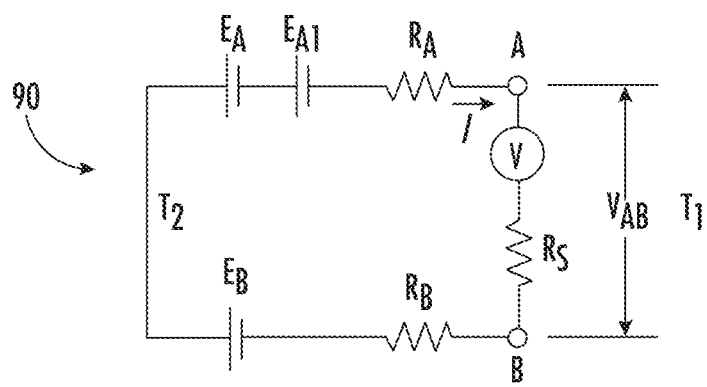
FIG. 3 is a schematic diagram illustrating aspects of a detector circuit arrangement that may be used with one or more embodiments of the present invention.

Certain aspects of a preferred implementation of thermoelectric detector 90 can be explained with reference to FIG. 3. In this case, detector 90 utilizes the Seebeck effect in which a temperature dependent potential is generated by the formation of a bi-metal junction that is common to a class of temperature measuring sensors called thermocouples. The bi-metal junction is formed when two dissimilar metal wires are coupled by welding or other common connection methods. In a thermocouple, a temperature difference between the two ends of the connected wires produces a measurable voltage.

In this regard, voltage $E_A$ and resistance $R_A$ represent one electrical conductor of material type A (e.g., a base metal such as iron or copper). Similarly, $E_B$ and $R_B$ represent another electrical conductor of material type B (e.g., a noble metal or alloy such as nickel/chromium, platinum, etc.). $T_2$ is the junction formed by coupling material type A to type B at one end, which in the case of a thermocouple would often be considered the "hot" junction. $T_1$ is the junction formed by coupling material types A and B to measuring instrumentation at the other end, which in the case of a thermocouple would often be considered the "cold" junction. V is a voltage measuring device (e.g., a sampler) and $R_S$ is a known large resistance intended to minimize the effects of $R_A$ and $R_B$. In a thermocouple, the difference between $E_A$ and $E_B$ represents the magnitude of the temperature difference between $T_2$ and $T_1$.

In accordance with embodiments of the present invention, the known temperature response of the bi-metal junction is not important. For example, junctions $T_1$ and $T_2$ may both be equally exposed to the vapor environment in a way that both will experience substantially the same ambient temperature. In the presence of the corrosive substance, a galvanically impressed voltage develops as the base metal is activated by contact with an electrolyte substance within the vapor environment. (The electrolyte dispersed by evaporation within the closed confines of the UST or the like is the same substance responsible for corrosion in the fuel delivery system.) With the base metal as the positive lead, the impressed voltage produced by formation of the galvanic circuit (represented by $E_{A1}$) increases the overall voltage $V_{AB}$ at $T_1$. Because the voltages $E_A$ and $E_B$ are minimized (due to no temperature differential between $T_1$ and $T_2$), $E_{A1}$ can be easily detected.

Figure 4:
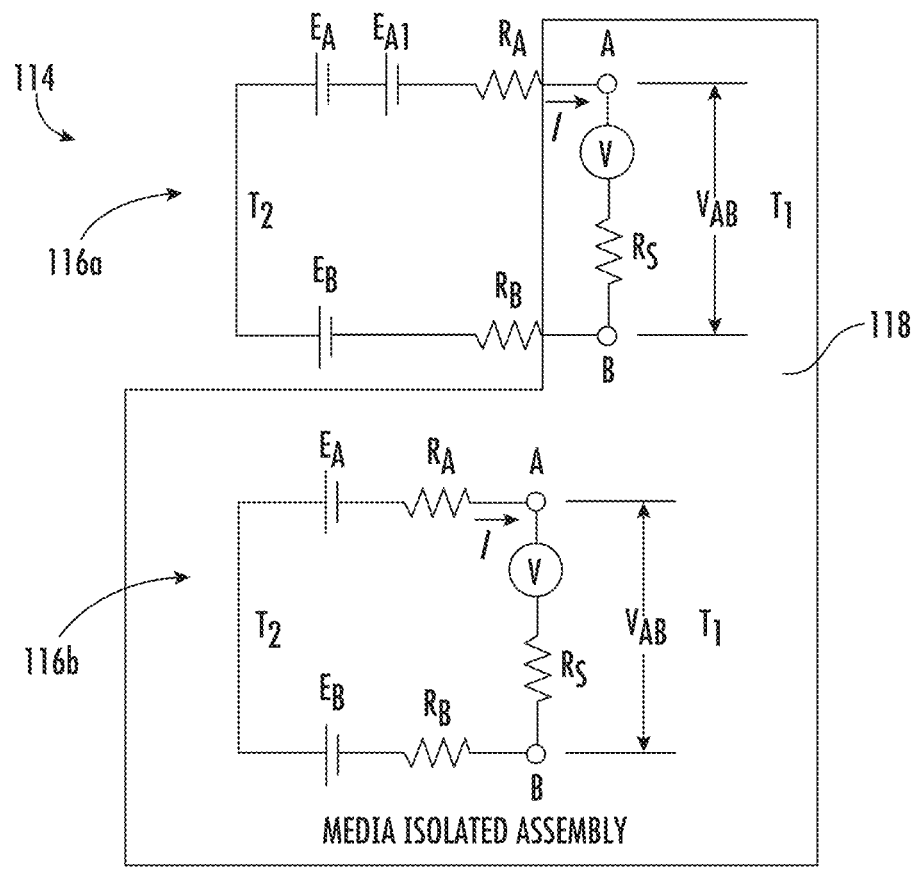
FIG. 4 is a schematic diagram illustrating aspects of a detector circuit arrangement that may be used with one or more embodiments of the present invention.

FIG. 4 illustrates an alternative thermoelectric detector 114 in accordance with the present invention, which can be used in lieu of detector 90. In this case, a pair of similar sensing circuits 116a and 116b are provided. Sensing circuits 116a and 116b are both arranged to experience the same ambient temperature (i.e., the temperature of the vapor environment), but only junction $T_2$ of sensing circuit 116a is directly exposed to the vapor environment. In this regard, sensing circuit 116b and junction $T_1$ of sensing circuit 116a are physically isolated from the vapor environment, such as by seals, covers, etc. As shown, for example, sensing circuit 116b and junction $T_1$ of sensing circuit 116a may be contained in a media isolated assembly 118 which allows measurement of the same temperature as junction $T_2$ of sensing circuit 116a without exposure to the vapor. As a result, only sensing circuit 116a will experience the galvanically impressed voltage $E_{A1}$. A simple comparison of the output voltage $V_{AB}$ of sensing circuits 116a and 116b can be used to determine whether $E_{A1}$ is nonzero.

Figure 5:
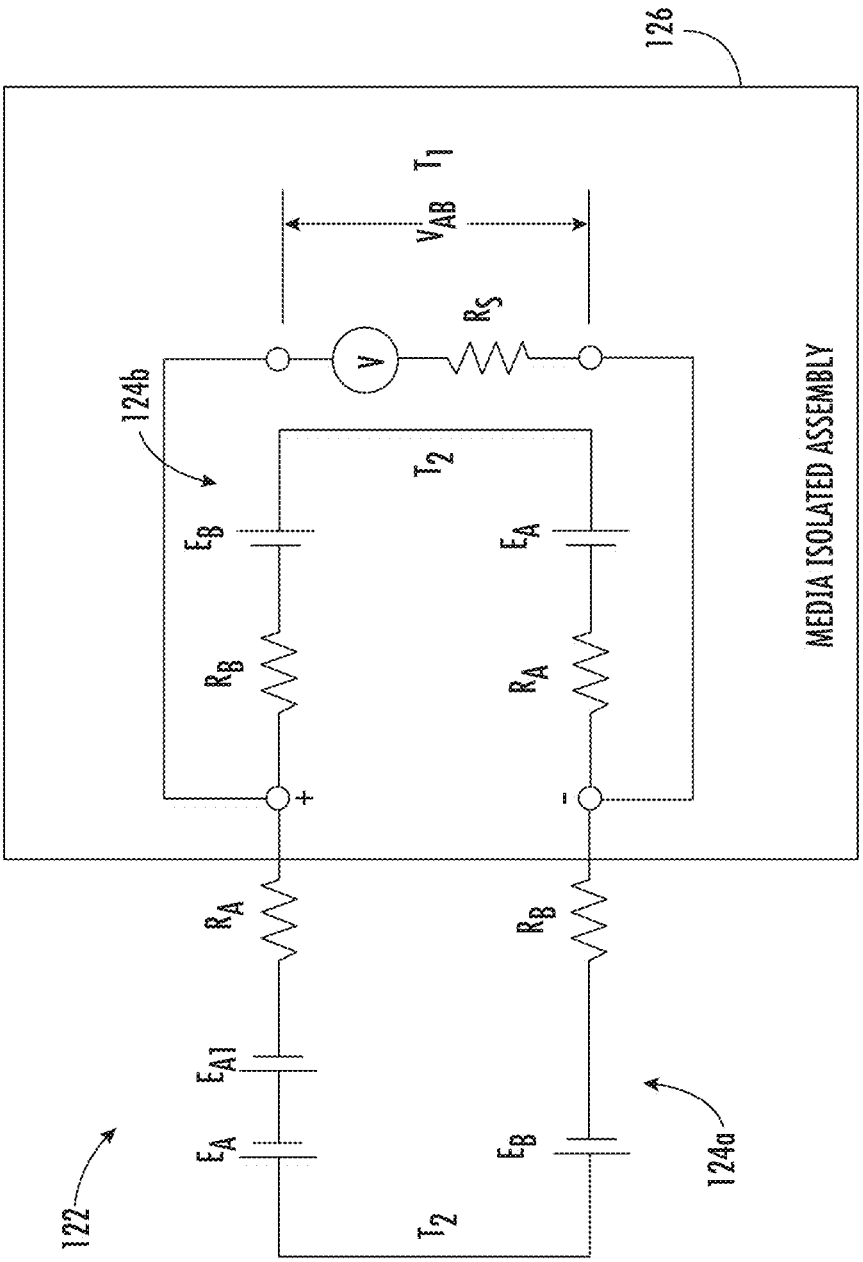
FIG. 5 is a schematic diagram illustrating aspects of a detector circuit arrangement that may be used with one or more embodiments of the present invention.

FIG. 5 illustrates an alternative thermoelectric detector 122 in accordance with the present invention, which can be used in lieu of detector 90. In this embodiment, a pair of similar sensing circuits 124a and 124b are connected to share a common junction $T_1$. The common junction $T_1$ and junction $T_2$ of sensing circuit 124b are contained in a media isolated assembly 126. While only junction $T_2$ of sensing circuit 124a is directly exposed to the vapor environment, all junctions experience substantially the same temperature. As will be appreciated, $T_1$ is nonzero in this embodiment only when the base metal lead of sensing circuit 124a is in contact with the corrosive substance.

Figure 6:
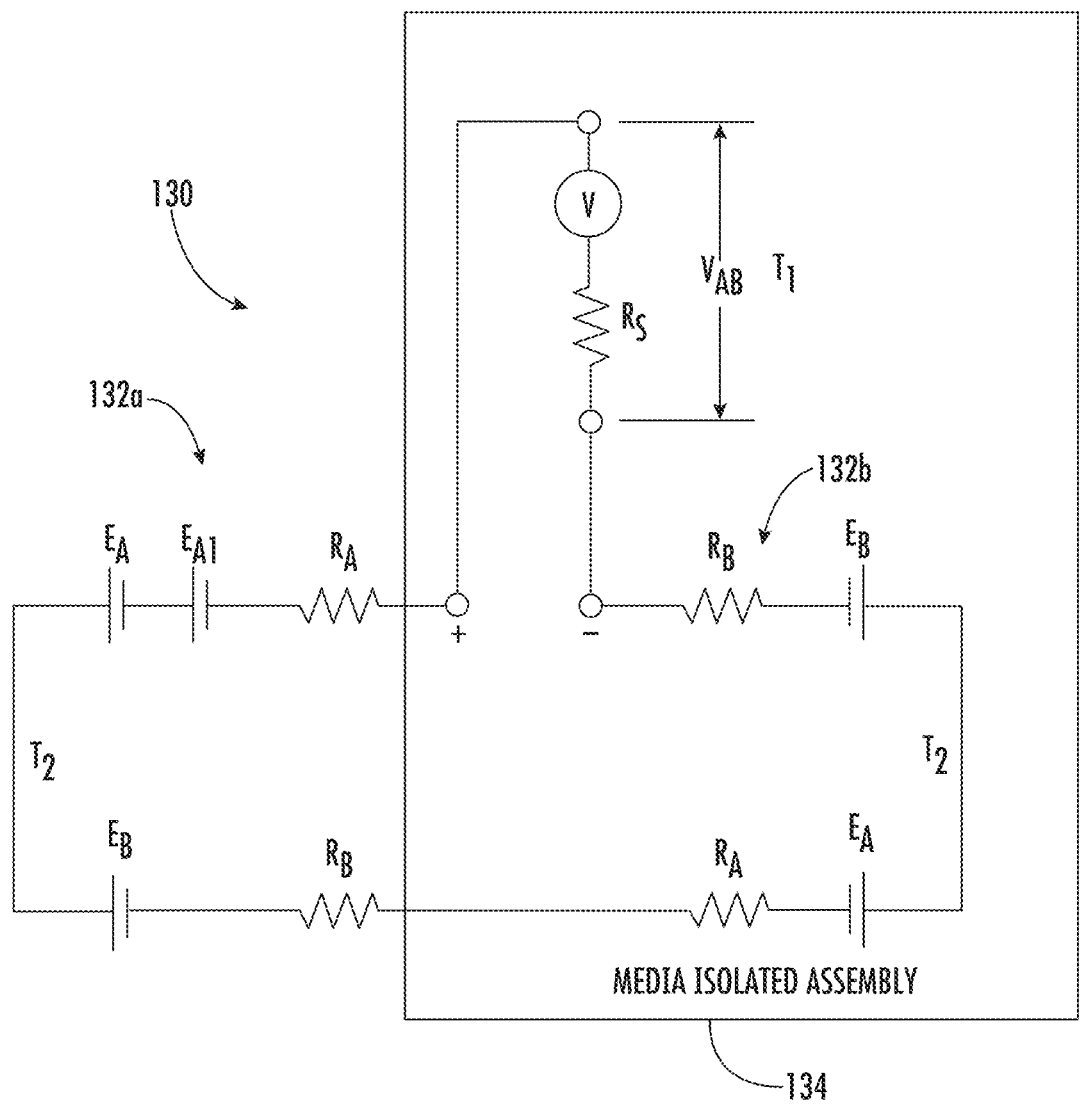
FIG. 6 is a schematic diagram illustrating aspects of a detector circuit arrangement that may be used with one or more embodiments of the present invention.

FIG. 6 illustrates an alternative thermoelectric detector 130 in accordance with the present invention, which can be used in lieu of detector 90. In this embodiment, a pair of similar sensing circuits 132a and 132b are connected together on their metal-type B sides. The voltage measuring device V and resistor $R_S$ are connected across the metal-type A sides of sensing circuits 132a and 132b to form a common junction $T_1$. The common junction $T_1$ and junction $T_2$ of sensing circuit 132b are contained in a media isolated assembly 134. While only junction $T_2$ of sensing circuit 132a is directly exposed to the vapor environment, all junctions experience substantially the same temperature. As will be appreciated, $T_1$ is nonzero in this embodiment only when the base metal lead of sensing circuit 132a is in contact with the corrosive substance.

Figure 7:
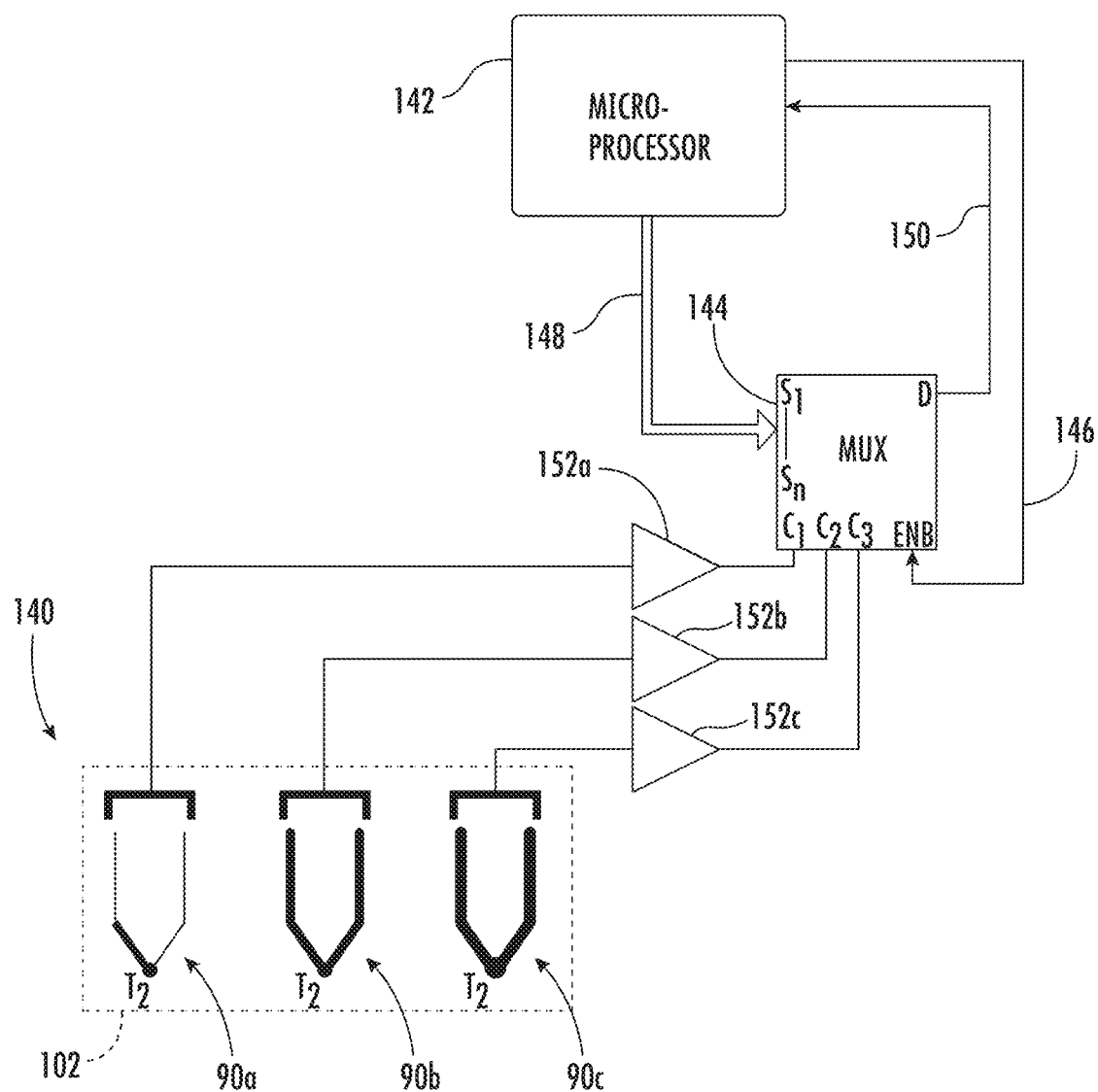
FIG. 7 is a diagrammatic representation illustrating aspects of a detector circuit arrangement that may be used with one or more embodiments of the present invention.

FIG. 7 illustrates another embodiment of a thermoelectric detector 140 in accordance with the present invention. In this case, detector 140 comprises a plurality of sensing circuits 90a, 90b, and 90c, each of which may be similar to detector 90 discussed above. In this regard, the sensing circuits 90a-c each have a respective bimetal junction $T_2$ exposed to the electrolytic vapor environment. Notably, however, wires forming the sensing circuits 90a-c have progressively heavier gage, such that 90b has heavier gage wire than 90a, and 90c has heavier gage wire than 90b. In the presence of a corrosive environment, each of the detection elements (sensing circuits) will experience corrosion at a detectably different rate. (Stated another way, the heavier gage wire has a slower detection response time than the lighter gage wire.) Because of the relationship between material mass and corrosive potential, for example the percentage of evaporated acetic acid, the time relationship between corrosion on each element provides a technique to evaluate the severity of the corrosive conditions.

In this embodiment, a microprocessor 142 is utilized to sample the outputs of sensing circuits 90a-c via a multiplexer ("MUX") 144. As one skilled in the art will appreciate from the above discussion, the functionality of microprocessor 142 and/or multiplexer 144 may in some cases be provided by suitable programming of tank monitor 72.) Microprocessor 142 enables operation of multiplexer 144 via a signal provided by line 146 to the multiplexer's "ENABLE" input. The outputs of the respective sensing circuits 90a-c are selected by microprocessor 142 via selection lines collectively designated 148. The signals on selection lines 148 (designated $S_1$ through $S_N$, with N being dependent on the number of sensing circuits in detector 140) inform multiplexer 144 which one of inputs $C_1$ through $C_3$ is active at any given time. The selected input is then provided at output D to microprocessor 142, e.g., via signal line 150. Inputs $C_1$ through $C_3$ are in electrical communication with the respective sensing circuits 90a through 90c. Respective amplifiers (or buffers) 152a, 152b, and 152c may be situated along the lines connecting sensing circuits 90a-c and their associated one of inputs $C_1$ through $C_3$, if necessary or desired. In operation, microprocessor 142 samples the outputs of sensing circuits 90a-c in rapid succession. The different detection readings of the sensing circuits 90a-c during any detection cycle, and the differences between the same sensing circuit 90a-c from one cycle to the next, is indicative of the severity of the corrosion.

Figure 8:
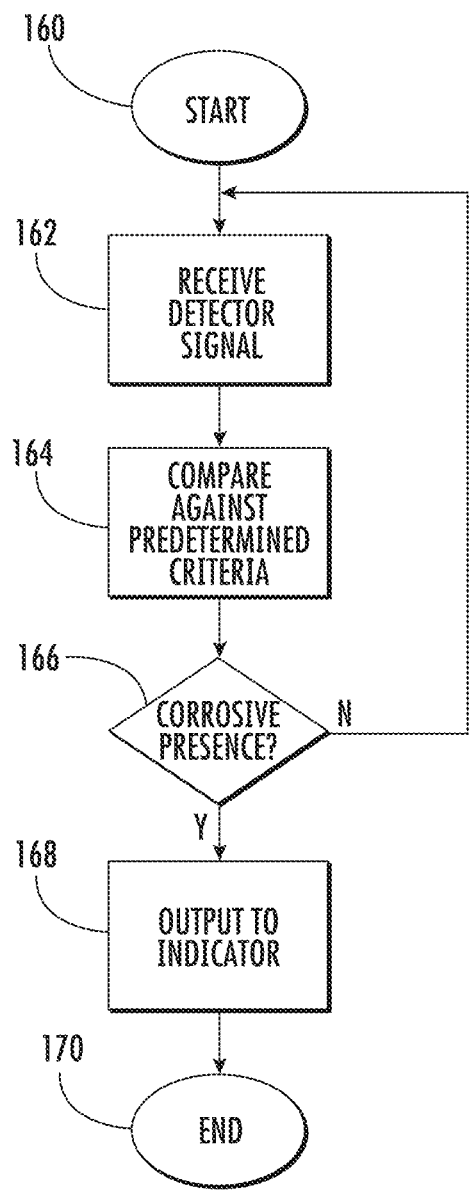
FIG. 8 is a flowchart illustrating certain aspects of the operation of a corrosive detection assembly in accordance with one or more embodiments of the present invention.

Referring now to FIG. 8, a method in accordance with the present invention of determining presence of a corrosive substance in a fuel dispensing system is illustrated. For example, the illustrated method may be practiced by program instructions running on the processor of tank monitor 72. After the process starts (as indicated at 160), detector signals (e.g., voltage signals from detector(s) 90) are received (as indicated at 162). This signal information is then compared against predetermined criteria (as indicated at 164). If the comparison shows presence of a corrosive and/or the severity of the corrosive (as indicated at step 166), an output is made to the indicator 112 (as shown at step 168). Otherwise, the process loops back for another comparison. The process ends at step 170.

It can thus be seen that embodiments of the present invention provide a fuel dispensing system with a novel corrosive detection assembly. While one or more preferred embodiments of the invention have been described above, it should be understood that any and all equivalent realizations of the present invention are included within the scope and spirit thereof. The embodiments depicted are presented by way of example only and are not intended as limitations upon the present invention. Thus, it should be understood by those of ordinary skill in this art that the present invention is not limited to these embodiments since modifications can be made. Therefore, it is contemplated that any and all such embodiments are included in the present invention as may fall within the scope and spirit thereof.

What is claimed is:

1. A fuel dispensing system comprising:
   a fuel tank adapted to contain a quantity of fuel;
   a fuel dispenser in fluid communication with said fuel tank via piping;
   a pump operative to transfer fuel from said fuel tank to said fuel dispenser; and
   a corrosive detection assembly operative to identify presence of a corrosive substance in said fuel, said corrosive detection assembly having:
      at least one thermoelectric detector positioned to be in contact with fuel vapor in said fuel dispensing system, said thermoelectric detector producing a detector signal indicating presence of the corrosive substance;
      wherein said thermoelectric detector comprises a sensing circuit having a pair of junctions formed by interconnection of dissimilar conductors, said pair of junctions being configured to experience a substantially equivalent ambient temperature with one of said pair of junctions configured to be exposed to the corrosive substance; and
      electronics in electrical communication with said thermoelectric detector, said electronics being operative to interpret said detector signal and produce an output if the corrosive substance is present.

2. A fuel dispensing system as set forth in claim 1, wherein said thermoelectric detector is located in an upper portion of the fuel tank above a maximum fuel level.

3. A fuel dispensing system as set forth in claim 1, wherein said pump is a submersible turbine pump (STP) and said thermoelectric detector is located in an STP sump.

4. A fuel dispensing system as set forth in claim 1, wherein said thermoelectric detector is located in a fuel dispenser sump located below said fuel dispenser.

5. A fuel dispensing system as set forth in claim 1, wherein said at least one thermoelectric detector comprises a plurality of thermoelectric detectors at different locations in said fuel dispensing system.

6. A fuel dispensing system as set forth in claim 1, wherein said one of said pair of junctions is in direct contact with the fuel vapor and another of said pair of junctions is in indirect contact with the fuel vapor via a media isolated assembly.

7. A fuel dispensing system as set forth in claim 6, wherein said detector signal originates at said another of said pair of junctions.

8. A fuel dispensing system as set forth in claim 7, further comprising a second sensing circuit having a pair of junctions formed by interconnection of dissimilar conductors, one of said pair of junctions of said sensing circuit and one of said pair of junctions of said second sensing circuit being connected together.

9. A fuel dispensing system as set forth in claim 1, wherein a first of said dissimilar conductors comprises a metal selected from the group consisting of iron and copper.

10. A fuel dispensing system as set forth in claim 9, wherein a second of said dissimilar conductors comprises a noble metal.

11. A fuel dispensing system as set forth in claim 10, wherein said second of said dissimilar conductors comprises platinum.

12. A fuel dispensing system as set forth in claim 9, wherein said second of said dissimilar conductors comprises a nickel/chromium alloy.

13. A fuel dispensing system as set forth in claim 1, wherein said thermoelectric detector comprises a plurality of said sensing circuits, said sensing circuits each having different gage dissimilar conductors from other of said sensing circuits.

14. A fuel dispensing system as set forth in claim 1, wherein said electronics comprise an analog-to-digital converter operative to receive said detector signal in analog form and produce a digital output and comparator circuitry.

15. A fuel dispensing system as set forth in claim 14, wherein said comparator circuitry comprises a processor and memory.

16. A fuel dispensing system as set forth in claim 1, wherein at least a portion of said electronics are incorporated into a tank monitor device in electrical communication with a level gauge in said fuel tank.

17. A corrosive detection assembly for use in a fuel dispensing system, said corrosive detection assembly comprising:
   at least one thermoelectric detector positioned to be in contact with fuel vapor in said fuel dispensing system, said thermoelectric detector producing a detector signal indicating presence of a corrosive substance;
   said thermoelectric detector including a sensing circuit having a pair of junctions formed by interconnection of dissimilar conductors, said pair of junctions being configured to experience a substantially equivalent ambient temperature with one of said pair of junctions configured to be exposed to the corrosive substance; and
   electronics in electrical communication with said thermoelectric detector, said electronics being operative to interpret said detector signal and produce an output if the corrosive substance is present.

18. A corrosive detection assembly as set forth in claim 17, wherein said one of said pair of junctions is in direct contact with the fuel vapor and another of said pair of junctions is in indirect contact with the fuel vapor via a media isolated assembly.

19. A corrosive detection assembly as set forth in claim 18, wherein said detector signal originates at said another of said pair of junctions.

20. A corrosive detection assembly as set forth in claim 18, further comprising a second sensing circuit having a pair of junctions formed by interconnection of dissimilar conductors, one of said pair of junctions of said sensing circuit and one of said pair of junctions of said second sensing circuit being connected together.

21. A corrosive detection assembly as set forth in claim 17, wherein a first of said dissimilar conductors comprises a metal selected from the group consisting of iron and copper.

22. A corrosive detection assembly as set forth in claim 21, wherein a second of said dissimilar conductors comprises a noble metal.

23. A corrosive detection assembly as set forth in claim 22, wherein said second of said dissimilar conductors comprises platinum.

24. A corrosive detection assembly as set forth in claim 22, wherein said second of said dissimilar conductors comprises a nickel/chromium alloy.

25. A corrosive detection assembly as set forth in claim 17, wherein said thermoelectric detector comprises a plurality of said sensing circuits, said sensing circuits each having different gage dissimilar conductors from other of said sensing circuits.

26. A corrosive detection assembly as set forth in claim 17, wherein said electronics comprise an analog-to-digital converter operative to receive said detector signal in analog form and produce a digital output and comparator circuitry.

27. A corrosive detection assembly as set forth in claim 26, wherein said comparator circuitry comprises a processor and memory.

* * * * *